United States Patent
Crawford et al.

(10) Patent No.: US 11,753,933 B2
(45) Date of Patent: Sep. 12, 2023

(54) SYSTEM AND METHODS FOR ESTIMATING SUBSURFACE HORIZONTAL PRINCIPAL STRESSES IN ANISOTROPIC FORMATIONS

(71) Applicant: ExxonMobil Technology and Engineering Company, Spring, TX (US)

(72) Inventors: Brian Crawford, The Woodlands, TX (US); William C. Reese, Cypress, TX (US); Jordan A. Freysteinson, Cypress, TX (US); Janelle M. Homburg, The Woodlands, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 0 days.

(21) Appl. No.: 17/650,922

(22) PCT Filed: Sep. 3, 2020

(86) PCT No.: PCT/US2020/070488
§ 371 (c)(1),
(2) Date: Feb. 14, 2022

(87) PCT Pub. No.: WO2021/087501
PCT Pub. Date: May 6, 2021

(65) Prior Publication Data
US 2023/0082833 A1    Mar. 16, 2023

Related U.S. Application Data

(60) Provisional application No. 62/928,790, filed on Oct. 31, 2019.

(51) Int. Cl.
*E21B 49/02* (2006.01)
*G01N 33/24* (2006.01)
(Continued)

(52) U.S. Cl.
CPC ............ *E21B 49/006* (2013.01); *E21B 21/08* (2013.01); *E21B 43/26* (2013.01); *E21B 49/06* (2013.01);
(Continued)

(58) Field of Classification Search
CPC ....... E21B 49/006; E21B 49/02; G01N 33/24; G01N 2203/0075
See application file for complete search history.

(56) References Cited

U.S. PATENT DOCUMENTS 5,838,633 A    11/1998 Sinha
6,609,067 B2    8/2003 Tare et al.
(Continued)

OTHER PUBLICATIONS

Amadei, B., W. Savage & H. Swolfs, "Gravitational stresses in anisotropic rock masses", Int. J. Rock Mech Min. Sci. & Geoech., 1987, vol. 24, No. 1, pp. 5-14.
(Continued)

*Primary Examiner* — Kenneth L Thompson
(74) *Attorney, Agent, or Firm* — ExxonMobil Technology and Engineering Company—Law Department

(57) ABSTRACT

A method for predicting a total minimum horizontal stress ($\sigma_h$) and a total maximum horizontal stress ($\sigma_H$) for an anisotropic formation may comprise: measuring Young's moduli parallel ±15° and perpendicular ±15° to a transverse isotropy plane of a horizontal core sample from the anisotropic subterranean formation; measuring Poisson's ratios parallel ±15° and perpendicular ±15° to the transverse isotropy plane of the horizontal core sample; inputting the measured Young's moduli and Poisson's ratios of the horizontal core sample into a 1-dimensional mechanical earth model (1-D MEM); and calculating, using the 1-D MEM, a predicted total minimum horizontal stress ($\sigma_h$) and a predicted total maximum horizontal stress ($\sigma_H$).

20 Claims, 4 Drawing Sheets

(51) Int. Cl.
  *E21B 49/00*  (2006.01)
  *E21B 21/08*  (2006.01)
  *E21B 43/26*  (2006.01)
  *E21B 49/06*  (2006.01)

(52) U.S. Cl.
  CPC ..... *G01N 33/24* (2013.01); *G01N 2203/0075* (2013.01)

(56) References Cited

U.S. PATENT DOCUMENTS

| | | | |
|---|---|---|---|
| 6,714,873 | B2 | 3/2004 | Bakunlin et al. |
| 6,904,365 | B2 | 6/2005 | Bratton et al. |
| 7,042,802 | B2 | 5/2006 | Sinha |
| 7,526,385 | B2 | 4/2009 | Sayers |
| 7,676,349 | B2 | 3/2010 | Xu et al. |
| 7,859,943 | B2 | 12/2010 | Herwanger |
| 7,953,587 | B2 | 5/2011 | Bratton et al. |
| 8,175,807 | B2 | 5/2012 | Sarez-Rivera et al. |
| 8,223,586 | B2 | 7/2012 | Pistre et al. |
| 8,619,500 | B2 | 12/2013 | Frederick |
| 8,967,249 | B2 | 3/2015 | Akkurt et al. |
| 9,157,318 | B2 | 10/2015 | Koepsell et al. |
| 9,223,041 | B2 * | 12/2015 | Wendt ................ G01V 1/306 |
| 9,303,508 | B2 | 4/2016 | Ramakrishnan et al. |
| 9,416,631 | B2 | 8/2016 | Wu et al. |
| 9,465,140 | B2 | 10/2016 | Crawford et al. |
| 9,983,106 | B2 * | 5/2018 | Han ........................ G01N 3/08 |
| 10,422,922 | B2 * | 9/2019 | Xu ........................ G01V 1/306 |
| 10,571,605 | B2 * | 2/2020 | Crawford ................ E21B 43/26 |
| 10,920,552 | B2 * | 2/2021 | Rodriguez Herrera ................... G01V 99/005 |
| 11,125,671 | B2 * | 9/2021 | Santagati .......... G01N 15/0826 |
| 2016/0290113 | A1 | 10/2016 | Kisra et al. |
| 2017/0023689 | A1 * | 1/2017 | Spence ................. G01V 1/284 |
| 2017/0235016 | A1 | 8/2017 | Prioul et al. |
| 2017/0321531 | A1 | 11/2017 | Far et al. |
| 2018/0030815 | A1 | 2/2018 | Eftekhari Far et al. |
| 2018/0058212 | A1 * | 3/2018 | Ali .......................... G01N 3/08 |
| 2018/0216441 | A1 | 8/2018 | Gu et al. |
| 2018/0238774 | A1 * | 8/2018 | Amendt ................ E21B 49/005 |
| 2019/0330981 | A1 | 10/2019 | Lei et al. |
| 2021/0190755 | A1 * | 6/2021 | Martysevich ........... G01N 33/24 |
| 2022/0206184 | A1 * | 6/2022 | Kumar ................... G06F 30/20 |

OTHER PUBLICATIONS

Amadei, B., "Importance of anisotropy when estimating and measuring in situ stresses in rock," Int. J. Rock Mech Min. Sci., 1996, vol. 33, No. 3, pp. 293-325.
Barree, R., J. Gilbert & M. Conway, "Stress and rock property profiling for unconventional reservoir simulation," SPE 118703, presented at the SPE Hydraulic Fracturing Technology Conference, Woodlands, TX, USA, Jan. 19-21, 2009, pp. 1-18.
Collins, P., Injection pressures for geomechanical enhancement of recovery processes in the Athabasca oil sands. SPE/Petroleum Society of CIM/CHOA 79028, presented at the SPE/PS-CIM/CHOA International Thermal Operations and Heavy Oil Symposium and International Horizontal Well Technology Conference, Calgary, Alberta, Canada, Nov. 4-7, 2002.
Crawford, B. et al., "Determining Static Elastic Anisotropy in Shales from Sidewall Cores: Impact on Stress Prediction and Hydraulic Fracture Modeling", Unconventional Resources Technology Conference, URTeC: 2206, Austin, Texas, Jul. 20-22, 2020, pp. 1-18.
Engelder, T., Stress Regimes in the Lithosphere, Chapter 5 Hydraulic Fracture, Princeton University Press, 1993, pp. 131-170.
Gholami, R., V. Rasouli, B. Aadnoy & R. Mohammadi, "Application of in situ stress estimation methods in wellbore stability analysis under isotropic and anisotropic conditions," J. Geophys. Eng., 2015, vol. 12, pp. 657-673.
Higgins, S., S. Goodwin, A. Donald, T. Bratton & G. Tracy. 2008. Anisotropic stress models improve completion design in the Baxter Shale. SPE 115736, presented at the SPE Annual technical Conference and Exhibition, Denver, CO, USA, Sep. 21-24, 2008.
Hornby, B., "Experimental laboratory determination of the dynamic elastic properties of wet, drained shales," J Geophys. Res., 1998, vol. 103, Issue B12, pp. 29945-29964.
Iverson, W., Closure stress calculations in anisotropic formations, SPE 29598, presented at the SPE Rocky Mountain Regional/Low Permeability Reservoirs Symposium, Denver, CO, USA, Mar. 20-22, 1995.
Johnson, P. & P. Rasolofosaon, "Nonlinear elasticity and stress-induced anisotropy in rock," J. Geophys. Res., 1996, vol. 101, Issue B12, pp. 3113-3124.
Mavko, G., T. Mukerji & J. Dvorkin, "Anisotropic form of Hooke's Law," The Rock Physics Handbook, Cambridge University Press, 2003, Chapter 2, pp. 19-26.
Melendez-Martinez, J. & D. Schmitt, "A comparative study of the anisotropic dynamic and static elastic moduli of unconventional reservoir shales: implication for geomechanical investigation," Geophysics, 2016, vol. 81, Issue 3, pp. D245-D261.
Norris, A. & B. Sinha, "Weak elastic anisotropy and the tube wave," Geophysics, 1993, vol. 58, Issue No. 8, pp. 1091-1098.
Savage, W., H. Swolfs & B. Amadei, "On the state of stress in the near-surface of the earth's crust," Pure and Applied Geophysics, 1992, vol. 138, No. 2, pp. 207-228.
Schoenberg, M., F. Muir & C. Sayers, "Introducing Annie: A simple three-parameter anisotropic velocity model for shales," Journal of Seismic Exploration, 1996, vol. or Chapter 5, pp. 35-49.
Thiercelin, M. & R. Plumb, "Core-based prediction of lithologic stress contrasts in East Texas Formations," SPE Formation Evaluation, Dec. 1994, pp. 251-258.
Thomsen, L., "Weak elastic anisotropy," Geophysics, 1986, vol. 51, No. 10, pp. 1954-1966.
Vernik, L. & A. Nur, "Ultrasonic velocity and anisotropy of hydrocarbon source rocks," Geophysics, 1992, vol. 57, Issue 5, pp. 727-735.
Wang, Z., "Seismic anisotropy in sedimentary rocks, part 1: a single-plug laboratory study," Geophysics, 2002, vol. 67, No. 5, pp. 1415-1422.
Waters, G., R. Lewis & D. Bentley, "The effect of mechanical properties anisotropy in the generation of hydraulic fractures in organic shales," SPE 146776, presented at the SPE Annual technical Conference and Exhibition, Denver, CO, USA, Oct. 30-Nov 2. 2011.
Wong, R., D. Schmitt, D. Collis & R. Gautam, "Inherent transversely isotropic elastic parameters of over-consolidated shale measured by ultrasonic waves and their comparison with static and acoustic in situ log measurements," J. Geophys. Eng. 2008, vol. 5, pp. 103-117.
Yale, D. & Swami, V., "Conversion of dynamic mechanical property calculations to static values for geomechanical modeling," ARMA 17-0644, presented at the 51st US Rock Mechanics / Geomechanics Symposium held in San Francisco, California, USA, Jun. 25-28, 2017.
Zoback, M., D. Moos & L. Mastin, "Well bore breakouts and in situ stress" J. Geophys. Res., 1985, vol. 90, No. B7, pp. 5523-5530.
Nejati, Morteza et al., A methodology to determine the elastic properties of anisotropic rocks from a single uniaxial compression test, Journal of Rock Mechanics and Geotechnical Engineering, 2019, vol. 11, pp. 1166-1183.
De Gennaro, V., Integrated unconventional gas evaluation workflow: from anisotropic geomechanical modelling to completion design, SPE 167735, 2014, pp. 1-16.

* cited by examiner

SYSTEM AND METHODS FOR ESTIMATING SUBSURFACE HORIZONTAL PRINCIPAL STRESSES IN ANISOTROPIC FORMATIONS

CROSS REFERENCE TO RELATED APPLICATION

This application claims the benefit of U.S. Provisional Application No. 62/928,790, filed Oct. 31, 2019, and priority to PCT/US2020/070488, filed Sep. 3, 2020, the disclosures of which are herein incorporated by reference in their entireties.

FIELD OF INVENTION

The present disclosure relates to systems and methods for estimating the subsurface principal stresses in anisotropic formations like shales.

BACKGROUND

Shales and other vertical transversely isotropic (VTI) formations have proven a valuable source of hydrocarbon. VTI formations have directionally dependent properties including permeability and stresses. Generally, while the vertical stress (stress acting perpendicular to the rock formations or strata) increases uniformly with depth as a consequence of the weight of the overlying strata, the (maximum and minimum) horizontal stresses (stresses acting perpendicular to the vertical stress and within the plane of the rock formations or strata) increase non-uniformly with depth as a result of complex interactions between mechanical rock properties and applied boundary conditions. The formation stresses can play an important role in well drilling, completion, stimulation, and abandonment and for optimizing the management of reservoirs throughout the production lifecycle. More specifically, the stresses can be used in one-dimensional mechanical earth models (1-D MEMs) of the subsurface. MEMs are a numerical representation of the state of stress and rock mechanical properties for a specific stratigraphic sections in a formation. 1-D MEMs are used for optimizing hydraulic fracture design and analysis in unconventional resources or for other additional drilling and subsurface applications associated with conventional reservoirs (e.g., wellbore stability, top seal integrity, cuttings reinjection, and the like).

Preferred methods for determining the magnitudes of subsurface horizontal stresses include: (i) direct measurement of total minimum horizontal stress ($\sigma_h$) using hydraulic fracturing techniques; and (ii) indirect back-calculation of total maximum horizontal stress ($\sigma_H$) from the borehole breakout angle and formation strength. In the event that insufficient direct and indirect data is available to determine horizontal stress magnitudes $\sigma_h$ and $\sigma_H$, several predictive techniques have been developed for estimating these values using various combinations of ultrasonic core velocity data, acoustic borehole logging data, 3-D surface reflection seismic data, and nonlinear acoustoelastic theory.

For example, formation in situ stress magnitudes can be estimated using a sonic borehole logging tool having a monopole source, a plurality of dipole sources and a plurality of detectors. The method comprises analyzing the flexural wave dispersions for dipole sources aligned parallel and perpendicular to the maximum far-field compressive stress direction together with the Stoneley wave dispersion derived from a monopole source, and performing a multi-frequency inversion of the flexural and Stoneley wave velocity dispersions over a selected frequency band to determine the principal stress magnitudes in the horizontal plane and the associated anisotropic elastic properties. A disadvantage of this technique is that it is inapplicable in the absence of the required borehole acoustic data. An alternative acoustic-based method for estimating subterranean horizontal stresses uses the anisotropic stiffness matrix, whereby at least one of the five required elastic coefficients in the subsurface formation is directly determined from either borehole- or core-based wave velocity measurements, and the remaining elastic coefficients are determined by assumption using theoretical relationships such as the "ANNIE" approximation.

In another example, a method and system for estimating the orientations and magnitudes of subsurface principal stresses can use 3-D surface reflection seismic data. The method includes receiving seismic data acquired over a region, receiving rock properties at a location within the region from core or borehole measurements, and estimating one or more stress characteristics by combining the seismic data and the rock properties using an effective medium theoretical relationship between the stress characteristics in the sub-region and anisotropic elastic stiffnesses and/or sonic velocities in the sub-region. However, this technique is inapplicable in the absence of seismic data.

In yet another example, core-derived ultrasonic velocity measurements can be used for direct determination of weak elastic anisotropy in VTI rocks in the lab. Traditionally three oriented core samples are required in order to assure that sufficient ultrasonic velocities are recorded for determination of the five dynamic moduli or stiffness constants ($C_{11}$, $C_{33}$, $C_{44}$, $C_{12}$, and $C_{13}$) required to estimate gravity- and deformation-induced minimum and maximum horizontal stress magnitudes. The three core samples are oriented with one parallel, one perpendicular, and one ±45° to the rotational symmetry axis of the VTI formation. Because of the specificity in and multitude of cores sample orientations, a full-diameter whole core must be retrieved from the subterranean formation of interest, which is an expensive and time consuming operation. Multiple techniques for analyzing the oriented core samples to derive the horizontal stresses have been developed. However, each technique is highly specialized and relies on either multiple piezoelectric transducer testing capabilities or complexly-machined prismatic samples, which can be impractical. Further, dynamic moduli measured in these procedures must then be converted to static values before implementation in the 1-D MEMs. However, dynamic moduli calculated using said techniques can differ significantly from the static values.

SUMMARY OF INVENTION

The present disclosure relates to systems and methods for estimating the subsurface principal stresses in VTI formations like shales utilizing horizontal core (e.g., sidewall core (SWC) samples) that are more readily obtained at less cost as compared to full-diameter whole core samples.

A first nonlimiting example method of the present disclosure comprises: measuring Young's moduli parallel ±15° and perpendicular ±15° to a transverse isotropy plane of a horizontal core sample from a subterranean formation; measuring Poisson's ratios parallel ±15° and perpendicular ±15° to the transverse isotropy plane of the horizontal core sample; inputting the measured Young's moduli and Poisson's ratios of the horizontal core sample into a 1-dimensional mechanical earth model (1-D MEM); and calculating, using the 1-D MEM, a predicted total minimum horizontal stress ($\sigma_h$) and a predicted total maximum horizontal stress ($\sigma_H$).

A second nonlimiting example method of the present disclosure comprises: measuring Young's moduli parallel ±15° and perpendicular ±15° to a transverse isotropy plane of a plurality of horizontal core samples from a subterranean formation at different vertical depths in the subterranean formation; measuring Poisson's ratios parallel ±15° and perpendicular ±15° to the transverse isotropy plane of the plurality of horizontal core samples; inputting the measured Young's moduli and Poisson's ratios of the plurality of horizontal core samples with the corresponding vertical depths into a 1-dimensional mechanical earth model (1-D MEM); and calculating, using the 1-D MEM, a predicted total minimum horizontal stress ($\sigma_h$) and a predicted total maximum horizontal stress ($\sigma_H$) as a function of the vertical depth A nonlimiting example computing device of the present disclosure comprises: a processor; a memory coupled to the processor; and instructions provided to the memory, wherein the instructions are executable by the processor to perform the first or second nonlimiting example method.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to systems and methods for estimating the subsurface principal stresses (e.g., total minimum horizontal stress ($\sigma_h$) and total maximum horizontal stress ($\sigma_H$)) in VTI formations based on the associated anisotropic static elastic properties, which may be measured using SWC samples recovered from the subsurface strata of interest. The subsurface principle stresses may then be used in earth models (e.g., 1-D MEMs).

Figure 1:
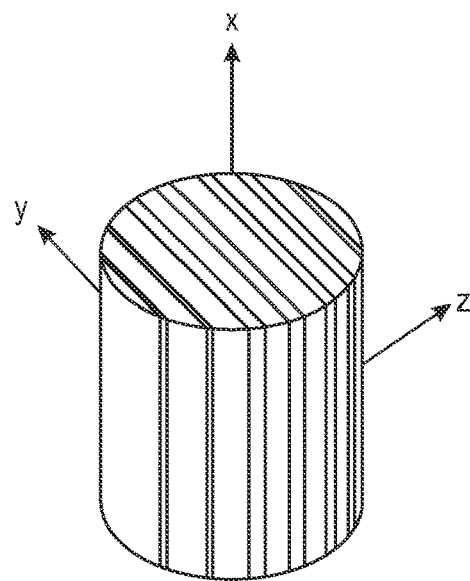
FIG. 1 illustrates a cylindrical core sample for a VTI formation with the axial direction being the labeled x-axis.

As used herein, a horizontal core sample refers to a core sample where the transverse isotropy plane of the strata from which the core sample is collected extends along the axial direction ±15° (or in some embodiments ±10°, or even within ±5°) of the horizontal core sample. For a cylindrical core sample, the axial direction of the core sample is along the length of the cylinder. FIG. 1 illustrates a cylindrical core sample for a VTI formation with the axial direction being the labeled x-axis.

Horizontal core samples can be collected directly from the formation as SWCs. Alternatively, if full-diameter whole core samples or other core samples are available, horizontal core samples may be collected from these other core samples. Advantageously, the systems and methods described herein can use SWC samples, which are more readily obtained and at a lower cost as compared to full-diameter whole core samples. In systems and methods according to certain embodiments, only horizontal core samples, and in particular only SWC samples, are needed (that is, such systems and methods may entail utilizing only a horizontal core sample and/or SWC (or multiple horizontal core samples and/or SWCs), without using any other type of core sample, such as vertical or whole core samples).

Further, the systems and methods described herein directly measure the static elastic moduli and eliminate the potential error associated with converting dynamic values to static values. Additionally, the systems and methods described herein are straightforward (a) not requiring acoustic data derived from seismic, borehole sonic, laboratory ultrasonic, or a combination of the three wave velocity data sources, which can be costly and time consuming to generate, and (b) not using data analyses incorporating complex, proprietary, tool dependent, nonlinear acoustoelastic theories relating principal stresses to dynamic elastic stiffnesses/velocities and their associated assumptions.

Geomechanic Relationships

Figure 2:
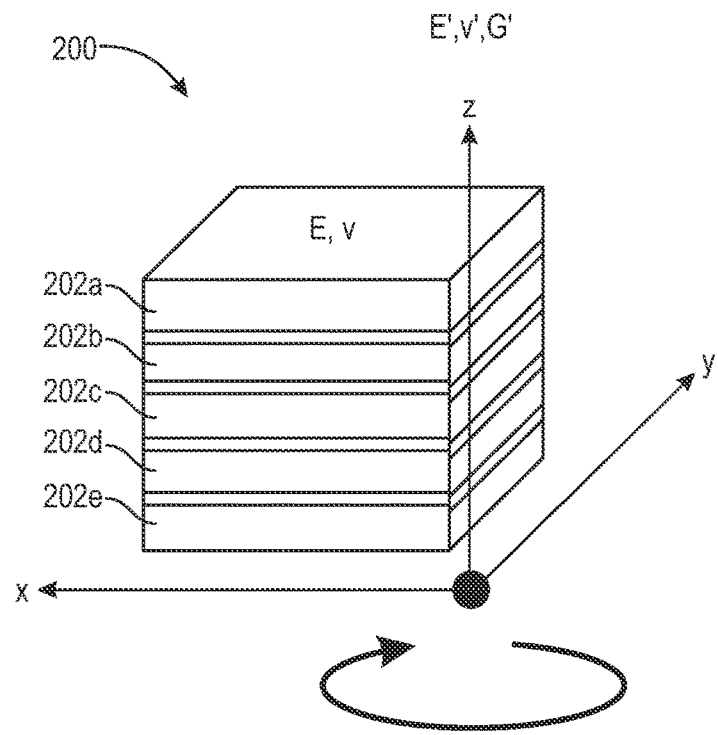
FIG. 2 is a representation of a VTI solid illustrating individual strata and a corresponding x,y,z-coordinate system.

FIG. 2 is a representation of a VTI solid 200 illustrating transverse isotropy planes 202a-202e and a corresponding x,y,z-coordinate system.

In the conventional solutions for predicting the magnitudes of in situ horizontal stresses, the earth's surface is assumed to be flat and the vertical stress acting in the z-direction is assumed to be known and given by gravity loading according to Equation (1):

$$\sigma_V + g\int_0^z \rho(z)dz \qquad (1)$$

where $\sigma_V$ represents the vertical total principal stress (preferably estimated from integration of a wireline density log) resulting from the geostatic load of the overlying strata or "overburden" at a subterranean vertical depth "z", $\rho(z)$ is formation density as a function of depth, and g is the gravitational constant.

Total horizontal principal stresses ($\sigma_h$ and $\sigma_H$) acting parallel to the x- and y-coordinate directions, respectively, are then calculated from theoretical considerations assuming all materials to be linearly elastic, and incorporating the combined effects of gravity, laterally constrained boundary conditions (both vanishing and finite horizontal deformations) and varying degrees of anisotropy dependent on formation elastic symmetry as shown schematically in FIG. 2.

For homogeneous, isotropic, linearly elastic solids (not illustrated), Equation (2) is Hooke's law generalized to three dimensions and expressed as a strain (both normal "$\varepsilon$" and shear "$\gamma$") and stress (both normal "$\sigma$" and shear "$\tau$") tensor matrix relationship in terms of commonly used engineering properties, Young's modulus "E" and Poisson's ratio "v".

$$\begin{Bmatrix} \varepsilon_x \\ \varepsilon_y \\ \varepsilon_z \\ \gamma_{yz} \\ \gamma_{xz} \\ \gamma_{xy} \end{Bmatrix} = \begin{Bmatrix} \frac{1}{E} & \frac{-v}{E} & \frac{-v}{E} & 0 & 0 & 0 \\ \frac{-v}{E} & \frac{1}{E} & \frac{-v}{E} & 0 & 0 & 0 \\ \frac{-v}{E} & \frac{-v}{E} & \frac{1}{E} & 0 & 0 & 0 \\ 0 & 0 & 0 & \frac{2(1+v)}{E} & 0 & 0 \\ 0 & 0 & 0 & 0 & \frac{2(1+v)}{E} & 0 \\ 0 & 0 & 0 & 0 & 0 & \frac{2(1+v)}{E} \end{Bmatrix} \begin{Bmatrix} \sigma_x \\ \sigma_y \\ \sigma_z \\ \tau_{yz} \\ \tau_{xz} \\ \tau_{xy} \end{Bmatrix} \quad (2)$$

The deformations of such isotropic, linearly elastic solids (in which all planes and axes are ones of elastic symmetry) can be calculated for known increments of stress by specifying only the following: (i) 1× Young's modulus, $E=E_x=E_y=E_z$; (ii) 1× Poisson's ratio, $v=v_{yx}=v_{zx}=v_{zy}$ where "$v_{ij}$" determines the ratio of strain in the j-direction to the strain in the i-direction due to a stress in the i-direction; and (iii) with Shear moduli, $G_{yz}=G_{xz}=G_{xy}=E/2(1+v)$.

In Equation (2), the vertical overburden stresses can be equated ($\sigma_z=\sigma_V=\rho gz$), and the minimum and maximum horizontal stresses can be equated ($\sigma_x=\sigma_h$ and $\sigma_y=\sigma_H$, respectively). Taking all shear stresses as zero and assuming constant horizontal strain boundary conditions such that $\varepsilon_x=\varepsilon_h$ and $\varepsilon_y=\varepsilon_H$ acting in the $\sigma_h$ and $\sigma_H$ directions respectively, the corresponding and well-known expressions for induced horizontal stresses (without proof) are: Equation (3) for a uniaxial strain assumption (zero horizontal deformations, $\varepsilon_h=\varepsilon_H=0$); and Equations (4) and (5) for a small horizontal deformation assumption (finite strains, $\sigma_h$ and $\sigma_H$ typically <5%).

$$\sigma_h = \sigma_H = \frac{v}{(1-v)}\sigma_V \quad (3)$$

$$\sigma_h = \frac{v}{(1-v)}\sigma_V + \frac{E}{(1-v^2)}(\varepsilon_h + v\varepsilon_H) \quad (4)$$

$$\sigma_H = \frac{v}{(1-v)}\sigma_V + \frac{E}{(1-v^2)}(\varepsilon_H + v\varepsilon_h) \quad (5)$$

Referring again to FIG. 2, or VTI linearly elastic solids (e.g., shales), the z-direction represents an axis of rotational symmetry, oriented perpendicular to the xy-plane of transverse isotropy (the TI-plane) in which elastic properties are isotropic. The equivalent matrix relationship between strains and stresses is given by Equation (6) with five independent elastic constants: (i) 2× Young's moduli parallel ±15° (or preferably ±10°, or more preferably ±5°) and perpendicular ±15° (or preferably ±10°, or more preferably ±5°) to the TI-plane, $E_x=E_y=E$ and $E_z=E'$; (ii) 2× Poisson's ratios parallel ±15° (or preferably ±10°, or more preferably ±5°) and perpendicular ±15° (or preferably ±10°, or more preferably ±5°) to the TI-plane, $v_{xy}=y_{yx}=v$ and $v_{zx}=v_{zy}=v'$; (iii) 1× shear modulus perpendicular to the TI-plane, $G_{yz}=G_{xz}=G'$ and $G_{xy}=E/2(1+v)$.

$$\begin{Bmatrix} \varepsilon_x \\ \varepsilon_y \\ \varepsilon_z \\ \gamma_{yz} \\ \gamma_{xz} \\ \gamma_{xy} \end{Bmatrix} = \begin{Bmatrix} \frac{1}{E} & -\frac{v}{E} & -\frac{v'}{E'} & 0 & 0 & 0 \\ -\frac{v}{E} & \frac{1}{E} & -\frac{v'}{E'} & 0 & 0 & 0 \\ -\frac{v'}{E'} & -\frac{v'}{E'} & \frac{1}{E'} & 0 & 0 & 0 \\ 0 & 0 & 0 & \frac{1}{G'} & 0 & 0 \\ 0 & 0 & 0 & 0 & \frac{1}{G'} & 0 \\ 0 & 0 & 0 & 0 & 0 & \frac{2(1+v)}{E} \end{Bmatrix} \begin{Bmatrix} \sigma_x \\ \sigma_y \\ \sigma_z \\ \tau_{yz} \\ \tau_{xz} \\ \tau_{xy} \end{Bmatrix} \quad (6)$$

Equation 7 provides the corresponding expressions for gravity-induced horizontal stresses in a horizontally layered, VTI medium.

$$\sigma_h = \sigma_H = \frac{v_{xz}}{(1-v)}\sigma_V = \frac{E}{E'}\frac{v'}{(1-v)}\sigma_V \quad (7)$$

For uniaxial strain boundary conditions, where "$v_{xz}$" represents Poisson's ratio for out-of-plane strain response to in-plane stress, $v_{xz}=y_{yz}=(E/E')\cdot v'$, which results in Equations (8) and (9).

$$\sigma_h = \frac{E}{E'}\frac{v'}{(1-v)}\sigma_V + \frac{E}{(1-v^2)}(\varepsilon_h + v\varepsilon_H) \quad (8)$$

$$\sigma_H = \frac{E}{E'}\frac{v'}{(1-v)}\sigma_V + \frac{E}{(1-v^2)}(\varepsilon_H + v\varepsilon_h) \quad (9)$$

For finite strain boundary conditions, Equations (3)-(5) and Equations (7)-(9) reduce to the uniaxial strain formulation when lateral strains resulting from tectonics vanish. Also, by comparing Equations (3) and (7), it is apparent that the inclusion of anisotropy serves to broaden the potential range for predicted horizontal stresses in lithologies such as shales, compared with the isotropic assumption.

The systems and methods of the present disclosure use the foregoing relationships and directly measured stress/strain data to derive $\sigma_h$ and $\sigma_H$, which can be used in various earth models.

Figure 3A:
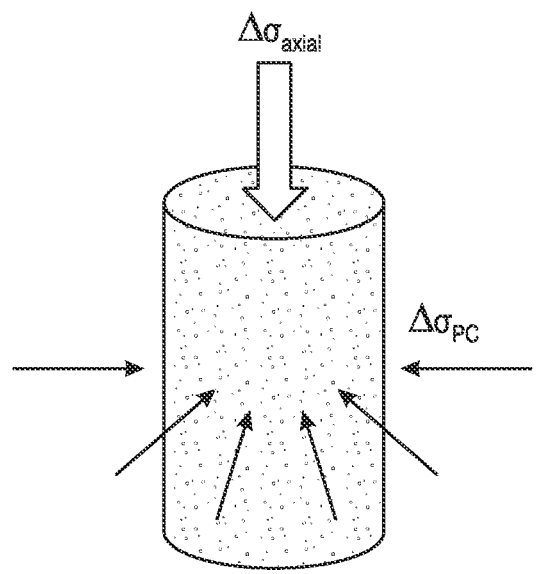
FIG. 3A illustrates a cylindrical sample subjected to a triaxially compressive stress state.
Figure 3B:
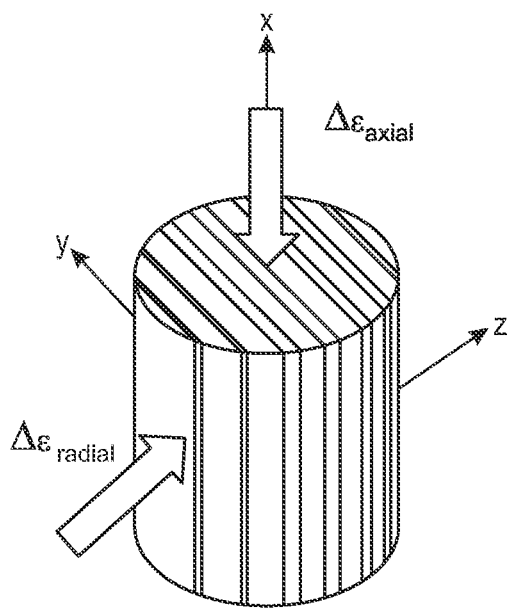
FIG. 3B illustrates a horizontal core sample from a VTI formation showing axial strain measured in the x-direction and radial strain (perpendicular to the transverse isotropy (TI) plane) measured in the z-direction.

FIG. 3A illustrates a cylindrical sample subjected to a triaxially compressive stress state. FIG. 3B illustrates a horizontal core sample from a VTI formation showing axial strain measured in the x-direction and radial strain (perpendicular to the transverse isotropy (TI) plane) measured in the z-direction.

In a FIG. 3A configuration, an axial load is applied to the specimen cross-sectional area such that an axial stress acts parallel to the cylinder long axis ("$\Delta\sigma_{axial}$" representing an increment of applied axial stress) and an independent axisymmetric confining pressure is applied to the sample circumference ("$\Delta\sigma_{PC}$" representing an increment of applied confining pressure). Correspondingly in FIG. 3B, horizontal core sample sourced from a VTI formation would be constrained to an orientation within a geomechanics testing apparatus. The axial strain would be measured along the x-direction ("$\Delta\varepsilon_{axial}$" representing an increment of resultant axial strain), and the radial strain as would be measured along the z-direction and perpendicular to the TI-plane ("$\Delta\varepsilon_{radial}$" representing an increment of resultant radial strain). Starting the analysis for homogeneous, isotropic, linearly elastic solids and by expressing Equation (2) in non-matrix, Equations (10)-(12) are derived.

$$\varepsilon_x = +\frac{\sigma_x}{E} - \frac{\nu\sigma_y}{E} - \frac{\nu\sigma_z}{E} \quad (10)$$

$$\varepsilon_y = -\frac{\nu\sigma_x}{E} + \frac{\sigma_y}{E} - \frac{\nu\sigma_z}{E} \quad (11)$$

$$\varepsilon_z = -\frac{\nu\sigma_x}{E} - \frac{\nu\sigma_y}{E} + \frac{\sigma_z}{E} \quad (12)$$

Equations (13)-(16) result when a laboratory-applied tri-axially compressive stress state is applied where the confining pressure is held constant so that $\Delta\sigma_y = \Delta\sigma_z = \Delta\sigma_{PC} = 0$ and the axial stress is varied where $\Delta\sigma_x = \Delta\sigma_{axial}$ are used as boundary conditions to Equations (10) and (12). Equations (14) and (16) represent the well-known definitions of Young's modulus "E" and Poisson's ratio "v", respectively.

$$\Delta\varepsilon_x = (1/E)(\Delta\sigma_{axial}) = \Delta\varepsilon_{axial} \quad (13)$$

$$E = \frac{\Delta\sigma_{axial}}{\Delta\varepsilon_{axial}} \quad (14)$$

$$\Delta\varepsilon_z = (1/E)(-\nu\Delta\sigma_{axial}) = \Delta\varepsilon_{radial} \quad (16)$$

$$\nu = -\frac{\Delta\varepsilon_{radial}}{\Delta\sigma_{axial}} \quad (17)$$

Alternatively, Equations (17)-(20) result when a laboratory-applied triaxially compressive stress state is applied where the axial stress is held constant so that $\Delta\sigma_x = \Delta\sigma_{axial} = 0$ and the confining pressure is varied where $\Delta\sigma_y = \Delta\sigma_z = \Delta\sigma_{PC}$, are used as boundary conditions to Equations (10) and (12).

$$\Delta\varepsilon_x = (1/E)(-2\nu\Delta\sigma_{PC}) = \Delta\varepsilon_{axial} \quad (17)$$

$$\Delta\varepsilon_z = (1/E)[\Delta\sigma_{PC}(1-\nu)] = \Delta\varepsilon_{radial} \quad (18)$$

$$E = \frac{\Delta\sigma_{PC}}{\Delta\varepsilon_{radial}}(1-\nu) \quad (19)$$

$$\nu = \frac{\Delta\varepsilon_{axial}}{\Delta\varepsilon_{axial} - 2\Delta\varepsilon_{radial}} \quad (20)$$

For isotropic materials, "E" derived from Equations (14) and (19) and "v" derived using Equations (16) and (20) should give the same value for Young's modulus and Poisson's ratio, respectively, with any deviation from equivalency representing a direct measure of static elastic anisotropy. This analysis can be extended to VTI materials by expressing Equation (6) in the non-matrix form of Equations (21)-(23).

$$\varepsilon_x = +\frac{\sigma_x}{E} - \frac{\nu\sigma_y}{E} - \frac{\nu'\sigma_z}{E'} \quad (21)$$

$$\varepsilon_y = -\frac{\nu\sigma_x}{E} + \frac{\sigma_y}{E} - \frac{\nu'\sigma_z}{E'} \quad (22)$$

$$\varepsilon_z = -\frac{\nu'\sigma_x}{E'} - \frac{\nu'\sigma_y}{E'} + \frac{\sigma_z}{E'} \quad (23)$$

For a constant confining pressure with varying axial stress boundary condition, Equations (21) and (23) give Equations (24) and (25), which upon rearrangement can be expressed as Equations (26) and (27).

$$\Delta\varepsilon_x = (1/E)(\Delta\sigma_{axial}) = \Delta\varepsilon_{axial} \quad (24)$$

$$\Delta\varepsilon_z = (1/E')(-\nu'\Delta\sigma_{axial}) = \Delta\varepsilon_{radial} \quad (25)$$

$$E = \frac{\Delta\sigma_{axial}}{\Delta\varepsilon_{axial}} \quad (26)$$

$$\frac{\nu'}{E'} = -\frac{\Delta\varepsilon_{radial}}{\Delta\sigma_{axial}} \quad (27)$$

Whereas, for a constant axial stress with varying confining pressure boundary condition, Equations (21) and (23) give Equations (28) and (29), which upon rearrangement can be expressed as Equations (30)-(32).

$$\Delta\varepsilon_x = -\Delta\sigma_{PC}(\nu/E + \nu'/E') = \Delta\varepsilon_{axial} \quad (28)$$

$$\Delta\varepsilon_z = (1/E')[\Delta\sigma_{PC}(1-\nu')] = \Delta\varepsilon_{radial} \quad (29)$$

$$\frac{\nu}{E} = \frac{-\Delta\varepsilon_{axial}}{\Delta\sigma_{PC}} - \frac{\nu'}{E'} \quad (30)$$

$$E' = \frac{\Delta\sigma_{PC}}{\Delta\varepsilon_{radial}}(1-\nu') \quad (31)$$

$$\therefore \nu' = \frac{\Delta\varepsilon_{axial} + \Delta\sigma_{PC}(\nu/E)}{\Delta\sigma_{PC}(\nu/E) + \Delta\varepsilon_{axial} - \Delta\varepsilon_{radial}} \quad (32)$$

The substitution of Equations (26) and (27) into (30) provides a direct solution for "v", substitution of Equation (30) into (32) provides a direct solution for "v'", and substitution of Equation (32) into (31) provides a direct solution for "E'". From these anisotropic static elastic moduli (E, E', v, v'), the horizontal principal stresses ($\sigma_h$ and $\sigma_H$) can be predicted.

Measuring the Static Elastic Moduli of Sidewall Core Samples

The static elastic moduli of horizontal core samples can be measured directly in the laboratory using a triaxial compression test system. Described herein is a nonlimiting example method for measuring the static elastic moduli of horizontal core samples. As many triaxial compression test systems cannot operate with confining pressures in excess of the applied axial stress, the preferred method described herein is accordingly constrained to always apply differential stress states with $\sigma_{axial}$ $\sigma_{PC}$, although it is recognized that this limitation need not always apply depending on equipment specifications.

Generally, through controlled incremental variation of the triaxially compressive stress state on a VTI horizontal core sample using specific boundary conditions the necessary anisotropic static elastic moduli (E, E', v, v') for horizontal principal stress prediction can be measured.

Figure 4A:
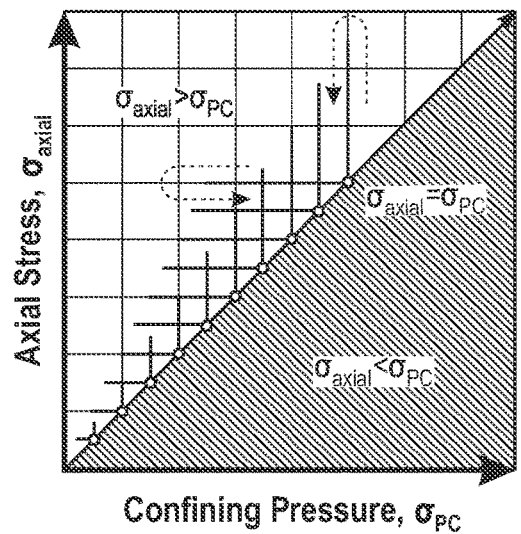
FIGS. 4A and 4B are schematic representations of triaxial compression test in confining pressure "$\sigma_{PC}$" versus axial stress "$\sigma_{axial}$" space for determination of anisotropic static elastic properties.
Figure 4B:
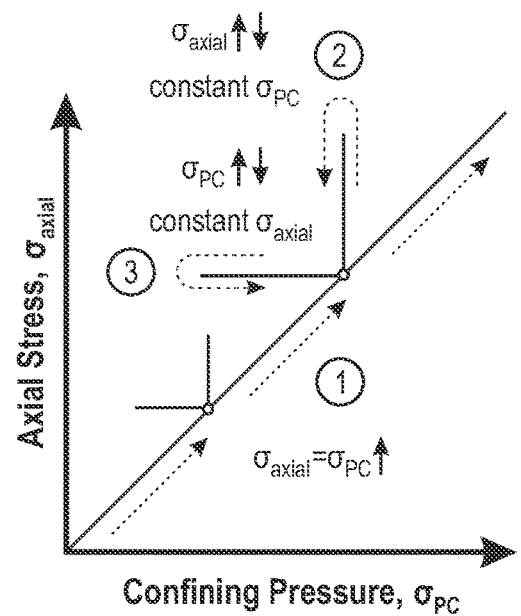

FIGS. 4A and 4B are schematic representations of a triaxial compression test in confining pressure "$\sigma_{PC}$" versus axial stress "$\sigma_{axial}$" space for determination of anisotropic static elastic properties. FIG. 4A shows an overview example of initial stress values (black dots) along the hydrostatic compression line where $\sigma_{axial} = \sigma_{PC}$.

Starting from initial stress values along the hydrostatic compression line, axial and radial strain measurements are taken for a constant confining pressure and as a consequence of an increase and then decrease in axial stress, which is represented by the vertical lines extending from the hydrostatic compression line. Also, axial and radial strain measurements are taken for a constant axial stress and as a consequence of a decrease and then increase in confining pressure, which is represented by the horizontal lines extending from the hydrostatic compression line.

FIG. 4B illustrates an example method for such measurements. In this example method, three distinct, consecutive, triaxially compressive stress paths are used in order to determine the required anisotropic static elastic properties: (1) synchronous increase in axial stress and confining pressure along the hydrostatic compression line; (2) ramp in axial stress (incremental increase then decrease) over a constant confining pressure; (3) ramp in confining pressure (incremental decrease then increase) over a constant axial stress. Stress path (1) is used to apply an initial hydrostatic stress state to the horizontal core where $\sigma_{axial}=\sigma_{PC}$. The magnitude of this applied hydrostatic stress can be chosen so as to replicate some approximation of the perceived in situ stress state associated with the subsurface formation of interest (for example an estimate of the effective overburden stress, or the in situ mean effective stress). Alternatively, as shown in FIG. 4B, a series of multiple values along the hydrostat can be used to determine the impact of relative stress magnitude on static elastic response.

Following attainment of an initial hydrostatic stress the horizontal core is then subjected to a series of controlled differential stress probes ($\sigma_{axial}-\sigma_{PC}>0$) in order to measure the resultant incremental axial and radial strain responses required to calculate static elastic anisotropy. Again, as many triaxial compression test systems cannot operate with confining pressures in excess of the applied axial stress, the preferred method is accordingly constrained to always apply differential stress states with $\sigma_{axial} \geq \sigma_{PC}$, although it is recognized that this limitation need not always apply depending on equipment specifications.

Figure 5A:
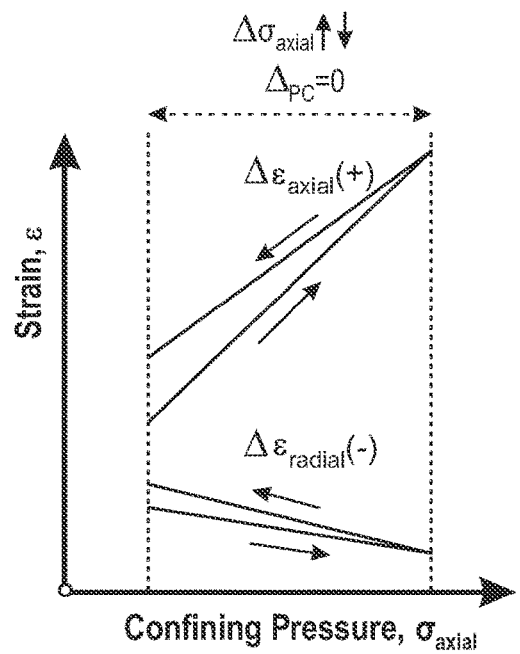
FIGS. 5A and 5B are representations of stress-strain curves for (a) varied axial stress and constant confining pressure and (b) varied confining pressure and constant axial stress, respectively.

Starting with application of a differential stress boundary condition in which axial stress is increased over a constant confining pressure, and as detailed in FIG. 4A, axial stress is ramped up by a fixed percentage of its value at initial hydrostatic conditions, and then ramped down by the same percentage amount back to the hydrostat. This results in measured axial and radial strain increments as shown schematically in FIG. 5A.

Figure 5B:
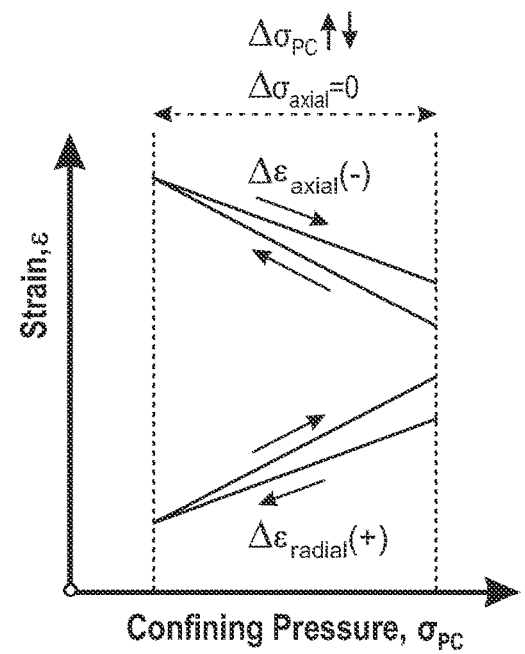

A subsequent differential stress boundary condition in which confining pressure is decreased over a constant axial stress is then applied as detailed in FIG. 4B, where confining pressure is ramped down by a fixed percentage of its initial value at hydrostatic conditions, and then ramped up again by the same percentage amount back to the hydrostat. This results in measured axial and radial strain increments as shown schematically in FIG. 5B. Preferably, the size of the percentage ramps should be equal for both axial stress- and confining pressure-varying differential stress phases. However, the order in which each differential stress phase is applied can be reversed. The magnitude of the percentage change applied (relative to the initial value under hydrostatic stress conditions) has to be sufficiently large to enable resolution of resultant strains in very stiff horizontal core samples, but sufficiently small to inhibit the onset of large-strain, non-recoverable plastic deformation in very compliant horizontal core samples, and is generally found to be around 10-40% approximately for most practical applications. All measured $\Delta\sigma_{axial}$, $\Delta\sigma_{PC}$, $\Delta\varepsilon_{axial}$, and $\Delta\varepsilon_{radial}$ increments can then be incorporated within the theoretical analyses in order to determine the necessary anisotropic static elastic moduli for horizontal principal stress prediction. If significant hysteresis in measured strains is observed as shown schematically in FIGS. 5A and/or 5B, then a calculation procedure can be applied to both loading and unloading phases in order to quantify any path dependent impact on measured elastic properties.

Methods and Systems

Figure 6:
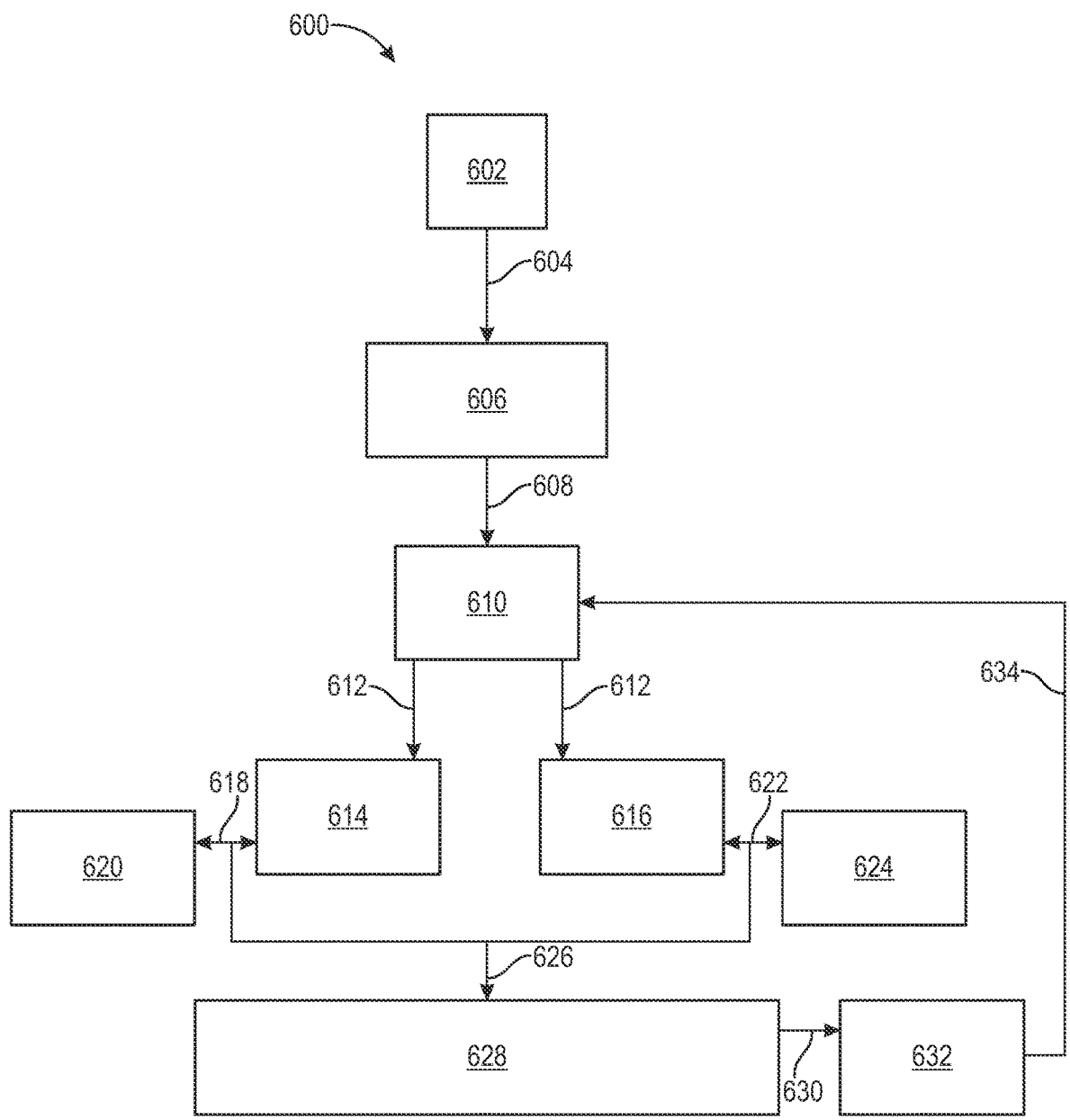
FIG. 6 is a diagram of a method of the present disclosure.

FIG. 6 is a diagram of a method 600 of the present disclosure. The method 600 includes obtaining a horizontal core sample 602 (a single horizontal core sample or multiple horizontal core samples, preferably from different depths, may be obtained, and in some embodiments, the horizontal sample(s) is/are one or more SWCs); and measuring/deriving 604 the static elastic properties 606 (E, E', v, v' using Equations (26), (31), substitutions of (8), and (32), respectively) of the horizontal core sample(s) (e.g., as described above). As noted above, the method 600 may be carried out without obtaining vertical and/or whole core samples, and/or by carrying out the measuring/deriving 604 only on horizontal core sample(s) without carrying out the measuring/deriving 604 on other types of samples (e.g., vertical or whole core samples). The static elastic properties 606 are then used as inputs for constructing 608 a 1-D MEM 610.

The 1-D MEM 610 can be built to use the measured properties one or more of a variety of ways. The measured/derived properties can be used directly, for example, as a function of true vertical depth for the corresponding horizontal core sample. Alternatively or additionally, the measured/derived properties can be correlated to other 1-D petrophysical properties derived from associated wireline log measurements (e.g., acoustic logs, NMR logs, and the like). Examples of 1-D petrophysical properties can include, but are not limited to, density, porosity, permeability, shale volume (i.e., volume fraction of clay), velocities, impedencies, dynamic moduli, and the like, and any combination thereof. For example, the measured properties may be correlated with shale volume as determined from the gamma ray log in order to derive a predictive function. Alternatively or additionally, the static measurements can be used to calibrate an existing 1-D MEM.

The method then includes predicting 612 the horizontal principal stresses $\sigma_h$ 614 and $\sigma_H$ 616 using the 1-D MEM 610 (e.g., using Equations (8) and (9), respectively). Here, the $\varepsilon_h$ and $\varepsilon_H$ terms in Equations (8) and (9) can be assumed to be 0.

As described relative to the horizontal core sample(s) 602 and corresponding static elastic properties 606, horizontal principal stresses $\sigma_h$ 614 and $\sigma_H$ 616 may be predicted for different portions of the formation based on where the horizontal core samples 602 were collected from.

The 1-D MEM 610 with the predicted horizontal principal stresses $\sigma_h$ 614 and $\sigma_H$ 616 may be used at this point (optionally with additional 1-D petrophysical properties) for managing hydrocarbons. As used herein, "managing hydrocarbons" or "hydrocarbon management" includes any one or more of the following: hydrocarbon extraction; hydrocarbon production, (e.g., drilling a well and prospecting for, and/or producing, hydrocarbons using the well; and/or, causing a well to be drilled, e.g., to prospect for hydrocarbons); hydrocarbon exploration; identifying potential hydrocarbon systems such as those including hydrocarbon-bearing formations; determining candidate-sampling locations within a hydrocarbon system; evaluating a hydrocarbon system; characterizing a hydrocarbon system such as a hydrocarbon-bearing formation; identifying well locations; determining well injection rates; determining well extraction rates; identifying reservoir connectivity; acquiring, disposing of, and/or abandoning hydrocarbon resources; reviewing prior hydrocarbon management decisions; and any other hydrocarbon-related acts or activities, such activities typically taking place with respect to a hydrocarbon system and/or subsurface formation. In particular embodiments, the 1-D MEM 610 may be used for modeling various hydrocarbon management operations, and methods may include managing hydrocarbons based upon such modeling. For example, the 1-D MEM 610 may be used for modeling and/or carrying out particular hydrocarbon management operations (e.g., hydraulic fracturing, drilling, and the like), and/or for modeling related properties (e.g., wellbore stability, top seal integrity, and the like) used in managing hydrocarbons.

In connection with particular embodiments, it is noted that maintaining the stability of a borehole in the subsurface is one of the most important goals of a drilling plan and is achieved through the design of a safe mud weight window and a drilling fluid pressure to keep the borehole stable. The drilling fluid pressure that maintains borehole stability is typically calculated from knowledge of the subsurface vertical stress magnitude, $\sigma_h$, $\sigma_H$, and a suitable formation failure criterion (e.g., criterion for formation tensile failure, criterion for formation compressive failure, and the like). If the drilling fluid pressure is too low then resultant borehole collapse can lead to operational problems and even more serious safety concerns. If the drilling fluid pressure is too high then resultant borehole fracturing can lead to significant drilling fluid losses.

In connection with further embodiments, managing hydrocarbons may include managing and/or carrying out hydraulic fracturing operations. Hydraulic fracturing is a commonly applied stimulation and/or well completion technique used to increase production from marginal and/or permeability challenged reservoirs. When created, hydraulic fractures in the subsurface propagate perpendicular to the least principal stress direction. Therefore, for unconventional shale reservoirs and other anisotropic formations, a horizontal well is typically drilled in the direction of minimum horizontal stress such that multiple transverse hydraulic fractures are initiated from the perforation clusters and propagate parallel to each other in the direction of the $\sigma_H$. Hydraulic fracture behavior in the vicinity of stratified rock formations is primarily influenced by variations in $\sigma_h$, whereby fracture height growth can be easily restricted if the layers above and below the target formation support higher stress than the reservoir rock. In addition, differences between the magnitudes of the $\sigma_h$ and $\sigma_H$ in a given layer can lead to variable hydraulic fracture complexity and thus production performance. Hydraulic fracture modeling takes into account $\sigma_h$ and $\sigma_H$. Where there is high contrast between $\sigma_h$ and $\sigma_H$, the stimulation creates a narrower, more planar fracture morphology. Conversely, where the stress contrast is low, wider more complex fracture geometry can result. Therefore, methods of the present disclosure can include modeling a hydraulic fracturing operation using the $\sigma_h$ and $\sigma_H$ determined by the methods described herein. Further, a hydraulic fracturing operation may be performed based on the results of said modeling.

In some instances, direct wellbore measurements of $\sigma_h$ and $\sigma_H$ may be available. A leak off test (LOT) is a direct measure of the $\sigma_h$. Formation microimaging (FMI) is a method for directly measuring the $\sigma_H$. If said direct measurements are available, the method 100 may include comparing 618 the predicted $\sigma_h$ 614 with the measured $\sigma_h$ 620 and comparing 622 the predicted $\sigma_H$ 616 with the measured $\sigma_H$ 624. Differences in the predicted and measured values can be used for deriving 626 the tectonic strain magnitudes 628 ($\varepsilon_h$ and $\varepsilon_H$) in Equations (8) and (9) and, consequently, for deriving 630 calibrated horizontal principal stress $\sigma_h$ and $\sigma_H$ terms 632, which can be input 634 into the 1-D MEM. This calibration process can be iteratively performed to arrive at a calibrated, depth varying 1-D MEM predictions of horizontal principal stress magnitudes. These, in turn, can also be used in managing hydrocarbons (e.g., as described above).

Further, over time, the downhole stresses can change. Accordingly, LOT and FMI measurements can be taken and new calibrated horizontal principal stress $\sigma_h$ and $\sigma_H$ terms 632 can be determined, which may be used to update the 1-D MEM 610. Such updated 1-D MEM 610 can be used in managing hydrocarbons, for example in managing drilling operations (e.g., to stay within same operating criteria, such as avoiding formation failure based on one or more formation failure criteria); and/or in managing hydraulic fracturing operations.

Various aspects of the systems and methods described herein utilize computer systems. Such systems and methods can include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and prior art-recognized equivalents and successor media, in which the software implementations embodying the present techniques are stored.

The methods described herein can, and in many embodiments must, be performed using computing devices or processor-based devices that include a processor; a memory coupled to the processor; and instructions provided to the memory, wherein the instructions are executable by the processor to perform the methods described herein (such computing or processor-based devices may be referred to generally by the shorthand "computer"). For example, any one or more of the following may be carried out using a computer: inputting measured Young's moduli and Poisson's ratios of horizontal core sample(s) into a 1-D MEM; calculating, using the 1-D MEM, a predicted total minimum horizontal stress and predicted total maximum horizontal stress; modeling hydrocarbon management operations (e.g., drilling operations and/or hydraulic fracturing operations); and the like. Indeed, in embodiments involving modeling hydrocarbon management operations, a computer must as a practical matter be employed for such modeling efforts. Similarly, any calculation, determination, derivation, or analysis recited as part of methods described herein will in may embodiments be carried out in whole or in part using a computer.

Furthermore, the instructions of such computing devices or processor-based devices can be a portion of code on a non-transitory computer readable medium. Any suitable processor-based device may be utilized for implementing all or a portion of embodiments of the present techniques, including without limitation personal computers, networks, personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

EXAMPLE EMBODIMENTS

A first nonlimiting example embodiment of the present disclosure is a method comprising: measuring Young's moduli parallel ±15° and perpendicular ±15° to a transverse isotropy plane of a horizontal core sample from a subterranean formation; measuring Poisson's ratios parallel ±15° and perpendicular ±15° to the transverse isotropy plane of the horizontal core sample; inputting the measured Young's moduli and Poisson's ratios of the horizontal core sample into a 1-dimensional mechanical earth model (1-D MEM); and calculating, using the 1-D MEM, a predicted total minimum horizontal stress ($\sigma_h$) and a predicted total maximum horizontal stress ($\sigma_H$).

A second nonlimiting example embodiment of the present disclosure is a method comprising: measuring Young's moduli parallel ±15° and perpendicular ±15° to a transverse isotropy plane of a plurality of horizontal core samples from a subterranean formation at different vertical depths in the subterranean formation; measuring Poisson's ratios parallel ±15° and perpendicular ±15° to the transverse isotropy plane of the plurality of horizontal core samples; inputting the measured Young's moduli and Poisson's ratios of the plurality of horizontal core samples with the corresponding vertical depths into a 1-dimensional mechanical earth model (1-D MEM); and calculating, using the 1-D MEM, a predicted total minimum horizontal stress ($\sigma_h$) and a predicted total maximum horizontal stress ($\sigma_H$) as a function of the vertical depth.

The first and second nonlimiting example methods may include one or more of the following: Element 1: the method further comprising: performing leak-off test and formation micro-imaging measurements on the subterranean formation; and calculating tectonic strain magnitudes based on the leak-off test and formation microimaging measurements, the $\sigma_h$, and the $\sigma_H$; Element 2: Element 1 and the method further comprising: inputting tectonic strain magnitudes into the 1-D MEM; Element 3: the method further comprising: correlating the measured Young's moduli and Poisson's ratios with at least one other 1-dimensional petrophysical property; Element 4: Element 3 and wherein the 1-dimensional petrophysical property is selected from the group consisting of: density, porosity, permeability, shale volume, velocities, impedencies, dynamic moduli, and any combination thereof; Element 5: wherein the Young's moduli parallel ±15° and perpendicular ±150 to the transverse isotropy plane are the Young's moduli parallel ±5° and perpendicular ±5° to the transverse isotropy plane, and wherein the Poisson's ratios parallel ±15° and perpendicular ±15° to the transverse isotropy plane are the Poisson's ratios parallel ±5° and perpendicular ±5° to the transverse isotropy plane; Element 6: wherein the horizontal core sample is a sidewall core sample; Element 7: the method further comprising: drilling a wellbore using a mud weight window and a drilling fluid pressure that is based on a subsurface vertical stress magnitude, the $\sigma_h$, the $\sigma_H$, and a formation failure criterion; and Element 8: the method further comprising: hydraulically fracturing the subterranean formation based on results from a hydraulic fracturing model that uses the $\sigma_h$ and the $\sigma_H$.

Examples of combinations include, but are not limited to, Element 1 (and optionally Element 2) in combination with Element 3 (and optionally Element 4); Element 7 or Element 8 in combination with one or more of Elements 1-6; Elements 5 and 6 in combination; and Element 5 and/or Element 6 in combination with one or more of Elements 1-4.

A third nonlimiting example embodiment of the present disclosure is a computing device comprising: a processor; a memory coupled to the processor; and instructions provided to the memory, wherein the instructions are executable by the processor to perform the first or second nonlimiting example method optionally with one or more of Elements 1-8.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method comprising:
   measuring Young's moduli parallel ±150 and perpendicular ±15° to a transverse isotropy plane of a horizontal core sample from a subterranean formation;
   measuring Poisson's ratios parallel ±15° and perpendicular ±15° to the transverse isotropy plane of the horizontal core sample;
   inputting the measured Young's moduli and Poisson's ratios of the horizontal core sample into a 1-dimensional mechanical earth model (1-D MEM); and
   calculating, using the 1-D MEM, a predicted total minimum horizontal stress ($\sigma_h$) and a predicted total maximum horizontal stress ($\sigma_H$).

2. The method of claim 1 further comprising:
   performing leak-off test and formation micro-imaging measurements on the subterranean formation; and
   calculating tectonic strain magnitudes based on the leak-off test and formation microimaging measurements, the $\sigma_h$, and the $\sigma_H$.

3. The method of claim 2 further comprising:
   inputting tectonic strain magnitudes into the 1-D MEM.

4. The method of claim 1 further comprising:
   correlating the measured Young's moduli and Poisson's ratios with at least one other 1-dimensional petrophysical property.

5. The method of claim 4, wherein the 1-dimensional petrophysical property is selected from the group consisting of: density, porosity, permeability, shale volume, velocities, impedencies, dynamic moduli, and any combination thereof.

6. The method of claim 1, wherein the Young's moduli parallel ±15° and perpendicular ±15° to the transverse isotropy plane are the Young's moduli parallel ±5° and perpendicular ±5° to the transverse isotropy plane, and wherein the Poisson's ratios parallel ±15° and perpendicular ±150 to the transverse isotropy plane are the Poisson's ratios parallel ±5° and perpendicular ±5° to the transverse isotropy plane.

7. The method of claim 1, wherein the horizontal core sample is a sidewall core sample.

8. The method of claim 1 further comprising:
   drilling a wellbore using a mud weight window and a drilling fluid pressure that is based on a subsurface vertical stress magnitude, the $\sigma_h$, the $\sigma_H$, and a formation failure criterion.

9. The method of claim 1 further comprising:
   hydraulically fracturing the subterranean formation based on results from a hydraulic fracturing model that uses the $\sigma_h$ and the $\sigma_H$.

10. A computing device comprising:
    a processor;
    a memory coupled to the processor; and
    instructions provided to the memory, wherein the instructions are executable by the processor to perform the method of any one of claims 1-9.

11. A method comprising:
    measuring Young's moduli parallel ±15° and perpendicular ±15° to a transverse isotropy plane of a plurality of horizontal core samples from a subterranean formation at different vertical depths in the subterranean formation;
    measuring Poisson's ratios parallel ±15° and perpendicular ±15° to the transverse isotropy plane of the plurality of horizontal core samples;
    inputting the measured Young's moduli and Poisson's ratios of the plurality of horizontal core samples with the corresponding vertical depths into a 1-dimensional mechanical earth model (1-D MEM); and
    calculating, using the 1-D MEM, a predicted total minimum horizontal stress ($\sigma_h$) and a predicted total maximum horizontal stress ($\sigma_H$) as a function of the vertical depth.

12. The method of claim 11 further comprising:
    performing leak-off test and formation micro-imaging measurements on the subterranean formation; and
    calculating tectonic strain magnitudes based on the leak-off test and formation microimaging measurements, the $\sigma_h$, and the $\sigma_H$.

13. The method of claim 12 further comprising:
    inputting tectonic strain magnitudes into the 1-D MEM.

14. The method of claim 11 further comprising:
    correlating the measured Young's moduli and Poisson's ratios with at least one other 1-dimensional petrophysical property.

15. The method of claim 14, wherein the 1-dimensional petrophysical property is selected from the group consisting of: density, porosity, permeability, shale volume, velocities, impedencies, dynamic moduli, and any combination thereof.

16. The method of claim 11, wherein the Young's moduli parallel ±150 and perpendicular ±15° to the transverse isotropy plane are the Young's moduli parallel ±5° and perpendicular ±5° to the transverse isotropy plane, and wherein the Poisson's ratios parallel ±15° and perpendicular ±15° to the transverse isotropy plane are the Poisson's ratios parallel ±5° and perpendicular ±5° to the transverse isotropy plane.

17. The method of claim 11, wherein the horizontal core sample is a sidewall core sample.

18. The method of claim 11 further comprising:
    drilling a wellbore using a mud weight window and a drilling fluid pressure that is based on a subsurface vertical stress magnitude, the $\sigma_h$, the $\sigma_H$, and a formation failure criterion.

19. The method of claim 11 further comprising:
    hydraulically fracturing the subterranean formation based on results from a hydraulic fracturing model that uses the $\sigma_h$ and the $\sigma_H$.

20. A computing device comprising:
a processor;
a memory coupled to the processor; and
instructions provided to the memory, wherein the instructions are executable by the processor to perform the method of claim 11.

\* \* \* \* \*